US006465225B1

(12) United States Patent
Fuhr et al.

(10) Patent No.: US 6,465,225 B1
(45) Date of Patent: Oct. 15, 2002

(54) METHOD AND DEVICE FOR MANIPULATING PARTICLES IN MICROSYSTEMS

(75) Inventors: Günter Fuhr; Rolf Hagedorn, both of Berlin (DE)

(73) Assignee: Evotec OAI AG (DE)

( * ) Notice: Subject to any disclaimer, the term of this patent is extended or adjusted under 35 U.S.C. 154(b) by 0 days.

(21) Appl. No.: 09/720,219

(22) PCT Filed: Jun. 28, 1999

(86) PCT No.: PCT/EP99/04468

§ 371 (c)(1),
(2), (4) Date: Feb. 22, 2001

(87) PCT Pub. No.: WO00/00816

PCT Pub. Date: Jan. 6, 2000

(30) Foreign Application Priority Data

Jun. 29, 1998 (DE) ........................................ 198 28 919
Nov. 20, 1998 (DE) ........................................ 198 53 658

(51) Int. Cl.[7] ........................ C12N 13/00; B01D 15/08; B01D 35/06; B03C 1/02; C02F 1/28

(52) U.S. Cl. ............................... 435/173.1; 210/198.3; 210/222; 210/223; 210/241; 210/658; 210/695

(58) Field of Search ............................. 210/198.3, 222, 210/223, 241, 658, 695; 435/173.1

(56) References Cited

U.S. PATENT DOCUMENTS

| | | | |
|---|---|---|---|
| 3,197,394 A | 7/1965 | McEuen | 204/186 |
| 3,674,198 A | 7/1972 | Eberle | 233/26 |
| 4,726,904 A | 2/1988 | Ayers | 210/658 |
| 4,764,473 A | 8/1988 | Matschke et al. | 435/287 |
| 4,804,355 A | 2/1989 | Brimhall et al. | 494/20 |
| 4,941,969 A | 7/1990 | Schonert et al. | 209/39 |
| 5,565,105 A | 10/1996 | Thakor | 210/695 |

FOREIGN PATENT DOCUMENTS

WO 9810869 3/1998

OTHER PUBLICATIONS

"Radio–Frequency Microtools for Particle and Live Cell Manipulation" by Muller et al.; (Natur WissenschaftenAufsatze 81, pp. 528–535 (1994).

"The LabCD™: A Centrifuge–Based Microfluidic Platform for Diagnostics" by Madou et al. (SPIE vol. 3259, 0277–786X/98, pp. 80–93.

G. Fuhr et al, "Radio–Frequency Microtools for Particle and Live Cell Manipulation", Naturwissenschaften, 1994, vol. 81, pp. 528–535.

M.J. Madou et al., The LabCD™: A Centrifuge–Based Microfluidic Platform for Diagnostics, SPIE, 1998, vol. 3259, pp. 80–93.

*Primary Examiner*—Christopher R. Tate
*Assistant Examiner*—Kailash C. Srivastava
(74) *Attorney, Agent, or Firm*—Baker Botts LLP

(57) ABSTRACT

For manipulation of particles in a fluidic microsystem (15) in which the particles are moved in a predetermined reference direction in a suspension liquid, the microsystem (15) is closed off at least at its end (17*a,* 17*b*) pointing to the reference direction. The particles move under the influence of centrifugal forces and/or gravitational forces in the suspension liquid which is stationary in relation to the microsystem (15), with the centrifugal forces and/or gravitational forces essentially extending parallel to the reference direction. Furthermore, the particles in the microsystem (15) are exposed to deflection forces whose direction differs from that of the reference direction. (FIG. 1).

15 Claims, 3 Drawing Sheets

METHOD AND DEVICE FOR MANIPULATING PARTICLES IN MICROSYSTEMS

The invention relates to a method for manipulating particles in fluidic microsystems, in particular for moving particles in microsystems along predetermined tracks, which are straight at least in sections, and devices for implementing such a method, in particular a fluidic microsystem in which synthetic or biological particles are manipulated in a suspension liquid, as well as applications of such a microsystem.

Fluidic microsystems with structures (e.g. channels) through which liquid flows, in which microelectrodes for influencing particles, (e.g. biological cells) through high-frequency fields on the basis of negative or positive dielectrophoresis are affixed to the channels through which liquid flows, have for example been described by G. Fuhr et al in "Naturwissenschaften", vol. 81, 1994, p. 528 ff.

Usually, a liquid flows through fluidic microsystems so as to move particles along. The microelectrodes attached to both the top and bottom of the longitudinal sides of the channel, result in compartmentalisation of the channel with high-frequency electrical fields by means of which the suspended particles can be deflected as desired, e.g. via branching out into adjacent channels or other structural elements. Above all the inflow of particles at one end of the channel and the setting of the flow speeds which as a rule are slow (some $\mu$l/h) are associated with difficulties which with increasing miniaturisation impose increasingly severe limitations.

A general disadvantage of conventional fluidic microsystems is due to the fact that directional and adjustable particle movement requires a solution flow whose control (e.g. flow speed) causes considerable problems.

From the publication by M. J. Madou et al. in "SPIE", volume 3259, 1998, p. 80 ff, a centrifugal flow-through system is known in which flows of liquid in a microsystem are not regulated with conventional pumps and valves, but instead under the influence of centrifugal forces. To this effect the microsystem is in a disc-like carrier in the shape of a CD-ROM disc. Analogous to the operation of CD storage media, the carrier is intended to be spun at high speed (ranging from 100 to 10,000 revolutions per minute). The liquids in the microsystem move radially outward under the influence of the centrifugal forces. Simultaneously to this liquid movement, certain biochemical reactions take place in the microsystem. It is also intended that the movement of liquid be utilised for conveying particles, as is the case in a conventional pumped flow of liquid.

The centrifugal technology according to M. J. Madou et al is associated with the following disadvantages. Both the achievement of sufficient movement of fluid and the achievement of conveyance of particles, which as far as is possible is free from any obstructions, in the liquid in the disk-shaped flat rotor, necessitates the above-mentioned high revolutions of the carrier. This results in a limitation of the conventional centrifugal force flow-through system to particular basic functions of traditional centrifuging or to achieving biochemical reactions. The above-mentioned microelectrode technique for generating high-frequency electrical fields in the microstructures cannot be applied. There is a further disadvantage relating to particle sorting and particle counting achieved with conventional centrifugal techniques. Such sorting and counting is possible only if the size of microchannels created corresponds to the size of the particles to be processed. Therefore, any given microsystem is always restricted to a particular particle size. In addition, when handling biological particles (cells, cell components) interactions quickly occur between the particles and the channel wall, causing blockages of the channel.

Furthermore, centrifuge systems are generally known in which the sample material in the centrifuge is not only subjected to centrifugal forces but in addition also to magnetic or electrical forces so as to achieve specific separation effects depending on the relationship between centrifugal forces and additional forces. These centrifuge systems cannot however be used to manipulate biological objects. Biological objects (e.g. cells) are handled in relatively highly conductive solutions or suspensions (conductivity ranges from approx. 0.5 to 3 Siemens/m). In the case of conventional centrifuge systems with relatively large electrode surfaces, such conductivity would result in undesirable heating-up phenomena. Conventional centrifuge systems are therefore limited to a conductivity of approx. 0.1 Siemens/m.

It is the object of the invention to provide an improved method for manipulating particles in fluidic microsystems, which method overcomes the disadvantages of traditional microsystems and provides an extended application range. Furthermore it is the object of the invention to provide an improved fluidic microsystem with directional particle movement which can be adjusted simply and with high accuracy. It is also the object of the invention to provide applications for such an improved microsystem.

These objects are solved by methods and devices with the characteristics according to claims 1 or 10. Advantageous embodiments and applications of the invention are defined in the dependent claims.

A first important aspect of the invention consists of moving from the traditional centrifugal flow-through system with moved liquids, to a method where in a fluidic microsystem under the influence of centrifugal forces, only the particles to be manipulated are moved, with essentially no liquid flows or movements occurring in the microsystem. To this effect a number of measures are realised which in particular comprise the use of a fluidic microsystem closed off at least on one side, the provision of such a microsystem on an oscillatory rotor centrifuge, and operation of this centrifuge at a predetermined rotational speed at which the particles in the microsystem move as desired.

The method according to the invention allows centrifugal action at low speeds. Due to the use of an oscillatory rotor system where the rotor as the carrier of the microsystem is vertically aligned (at standstill or low speed), moving to a horizontal alignment (at high speeds), as the speed decreases, gravity increasingly influences the movement of the particles in the microsystem. According to a further aspect of the invention a particle movement in microsystems which are closed off on at least one side is also described, which when at a standstill is vertically aligned relative to the microsystem. Particle movement takes place as sedimentation under the influence of gravity.

According to the invention, in particular those types of microsystems which comprise microelectrode devices for dielectrophoretic influencing of particle movement, are combined with the principle of centrifuging. As a result of the centrifugal forces, the suspended particles move through the microchannels or other microstructures in a microsystem in which they (without being able to exit) are for example separated, brought to a predetermined position, fused, sorted or permeated under the influence of electrical polarisation forces.

The invention provides an important advantage in that for the first time in the case of microsystems with a complex structure, involving dielectrophoretic particle influencing, there is no need to use pumps or valves which are difficult to control and subject to malfunction, without this resulting in any limitation in the functionality of the microsystem. There are no limitations in relation to the dimensions of the channel cross sections. There is an option of rotating the microsystem simultaneously together with the associated control electronics. Interactions between particles (in particular biological particles) and wall areas of the microsystem can easily be prevented. Conversely, with respective structuring, such interactions can be achieved in a predetermined way for investigating binding procedures.

The invention provides an important advantage in that all particles can be subjected to the same extent to centrifugal forces, and can move corresponding to a reference direction along predetermined channels, and separation e.g. in various sub-channels or reservoirs is exclusively achieved via deflection forces which act in a particle-specific way, independent of the centrifugal forces. The direction of the deflection forces differs from the reference direction, with the angular difference being preferably less than 90°. Only the particle speed is set via the centrifugal force.

After separation, the additional forces can be switched off without the particles mixing again. It is an unexpected and important characteristic that through the use of a swinging rotor centrifuge, the contact between particles and sample chamber walls can be prevented. This is of importance especially in the case of biological objects.

Details and further advantages of the invention are described below, with reference to the enclosed drawings, as follows.

The embodiments of the invention described here refer to a combination of a microsystem having a microelectrode arrangement for carrying out negative or positive dielectrophoresis (dielectrophoretic microsystem) comprising a swinging rotor centrifuge. Both the dielectrophoretic microsystem (apart from the channel structures capable of being closed off at least on one side) and the swinging rotor centrifuge are known per se. Consequently, their technical details are no further discussed here. It must be emphasised that in this document the term "swinging rotor centrifuge" is to be interpreted in the widest sense in that any centrifuge comprising at least one rotor which can be hinged upright depending on the speed, is included, which rotor itself forms the microsystem and the associated control system; into which rotor the microsystem and the associated control are integrated; or onto which rotor the microsystem and the respective control system are positioned.

The particles manipulated according to the invention can comprise synthetic particles or biological objects. The synthetic particles are for example membrane-surrounded formations such as liposomes or vesicles or so-called beads or also macromolecules. The biological objects comprise for example biological cells or components of such cells (e.g. cell organelles), bacteria or viruses. The particles can also be aggregates or agglomerations of such particles and/or objects. The invention is preferably implemented using cell-physiologically relevant or medically relevant fluids with a conductivity below 5 Siemens/m.

Figure 1:
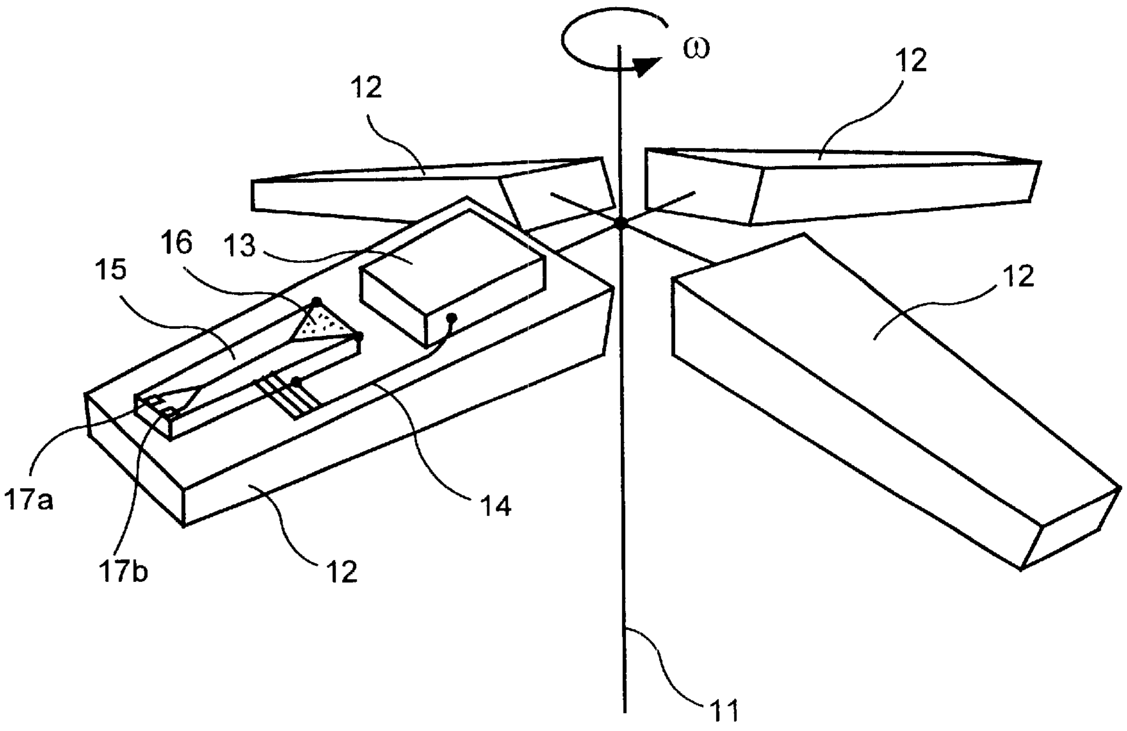
FIG. 1 shows a diagrammatic perspective view of the design of a centrifuge with a microsystem.

FIG. 1 is a diagrammatic overview of a device according to the invention for illustrating the affixation of a dielectrophoretic system to a centrifuge device.

A usual or application-dependent modified rotor of a centrifuge with axis of rotation 11 comprises four receptacles 12 into which the following are inserted so as to fit snugly and to tolerate the speeds applied: a microsystem 15 and control electronics 13 for controlling the microsystem with high-frequency alternating signals of different phase positions and amplitudes. The control electronics are connected to the microsystem 15 via cable 14, connector or otherwise. Preferably, the energy supply to the control device is via an electrical connection (rotation contact) with the stationary laboratory system. The microsystem comprises an input depot 16, the size of which can vary depending on the application, said depot 16 prior to centrifugation being filled with a particle suspension or cell suspension. From the input depot 16, a channel structure (details of which are provided below), extends to the collecting zones 17*a*, 17*b* which form an end of the microsystem 15 which end is closed at least during centrifuging. This means that the end of the microsystem can either be permanently closed off, or during standstill of the device can be opened by way of respective connection elements, and can be connected to predetermined additional systems for transferring the samples. The microsystem 15 is arranged on the retainer 12 such that during operation of the centrifuge (rotor turning around the axis of rotation 11 at a rotation frequency of ω), the centrifugal forces acting on the microsystem 15 and the particles located in said microsystem, are directed in the reference direction from the input depot 18 towards the collecting zones 17*a*, 17*b*. The retainers 12 are attached to the rotor (not shown) so as to be hingeable. With the centrifuge at a standstill, the retainers 12 are essentially aligned vertically or at a shallow angle in relation to the axis of rotation. During operation of the centrifuge, depending on the speed, the retainers 12 come up to a larger angle until they are aligned horizontally, i.e. perpendicular to the axis of rotation 11. Under the influence of gravity (with the centrifuge at a standstill) or the centrifugal forces, the particles flow through the electronically controlled microchannel system and congregate in the collection zones (e.g. at the closed end of the part of the microsystem pointing away from the rotor axis).

During this passage, the particles are treated according to predetermined programs (see below). Since the particles carry out various movements and assume various end positions depending on their density, the present invention combines the advantage of centrifugal separation and centrifugal movement with the possibilities of preprogrammable dielectrophoresis. Normally, negative dielectrophoresis of the particles is used; in exceptional cases also positive dielectrophoresis. Control of particle movement via rotational speed (ω) of the rotor 11 is a further advantage provided by the invention. Since in this case it is also possible to pass through programmable variations, a second complex of determinable parameters during particle manipulation is provided.

The centrifuge device comprises a rotational speed control (not shown) which provides a reproducible and precise speed adjustment in particular at low speeds. The rotational speed is selected application-specifically, depending on the desired speed of the particles to be manipulated and depending on the actual design of the centrifuge. For biological particles (e.g. cells), the interesting particle speeds are below approx. 500 μm/s (preferably ranging from 50 to 100 μm/s); for synthetic particles (e.g. latex beads) the speeds are higher (e.g. some m/s). The rotational speed of the centrifuge is selected according to the interrelationship between rotary speed and centrifugal force, depending on the size or density of the particles. The following information refers to a spacing of the microsystem from the rotor axis, ranging from 1 to 10 cm. For particle diameters ranging from 50 to 600 nm (e.g. viruses), rotational speeds can range from 1 to 1,000 rpm. In the case of particles with a diameter of approx. 5 μm, rotational speeds up to 100 rpm are preferred, but higher speeds can be set. In the case of particularly small particles, e.g. macromolecules, still higher rotational speeds can be realised. For biological cells, at a distance between the microsystem and the axis of rotation 11 of approx. 5 to 10 cm, speeds ranging from a few revolutions per minute to several hundred (e.g. 600) revolutions per minute result; preferably below 100 rpm. Achievable centrifugal forces are in the region of pN to nN. The centrifuge is however also designed for higher speeds which can be set in particular for small particles or for cleaning or rinsing purposes. These increased speeds can range up to the speeds of conventional laboratory centrifuges.

The rotational speed of the centrifuge is also selected depending on the dielectrophoretic forces acting on the particles in the microsystem. The dielectrophoretic forces as polarisation forces depend on the type and size of the particles. The speed is preferably selected so that the centrifugal forces acting on the particles are less than, or equal to, the dielectrophoretic forces. If these are not known, the speed can also be selected in relation to the following criterion. The particles must move slowly enough along the channel structure, so that sufficient time remains for dielectrophoretic deflection when they pass the microelectrode equipment. The effectiveness or ineffectiveness of dielectrophoretic deflection depending on rotational speed, can be acquired optically or electrically using suitable sensors.

Figure 2:
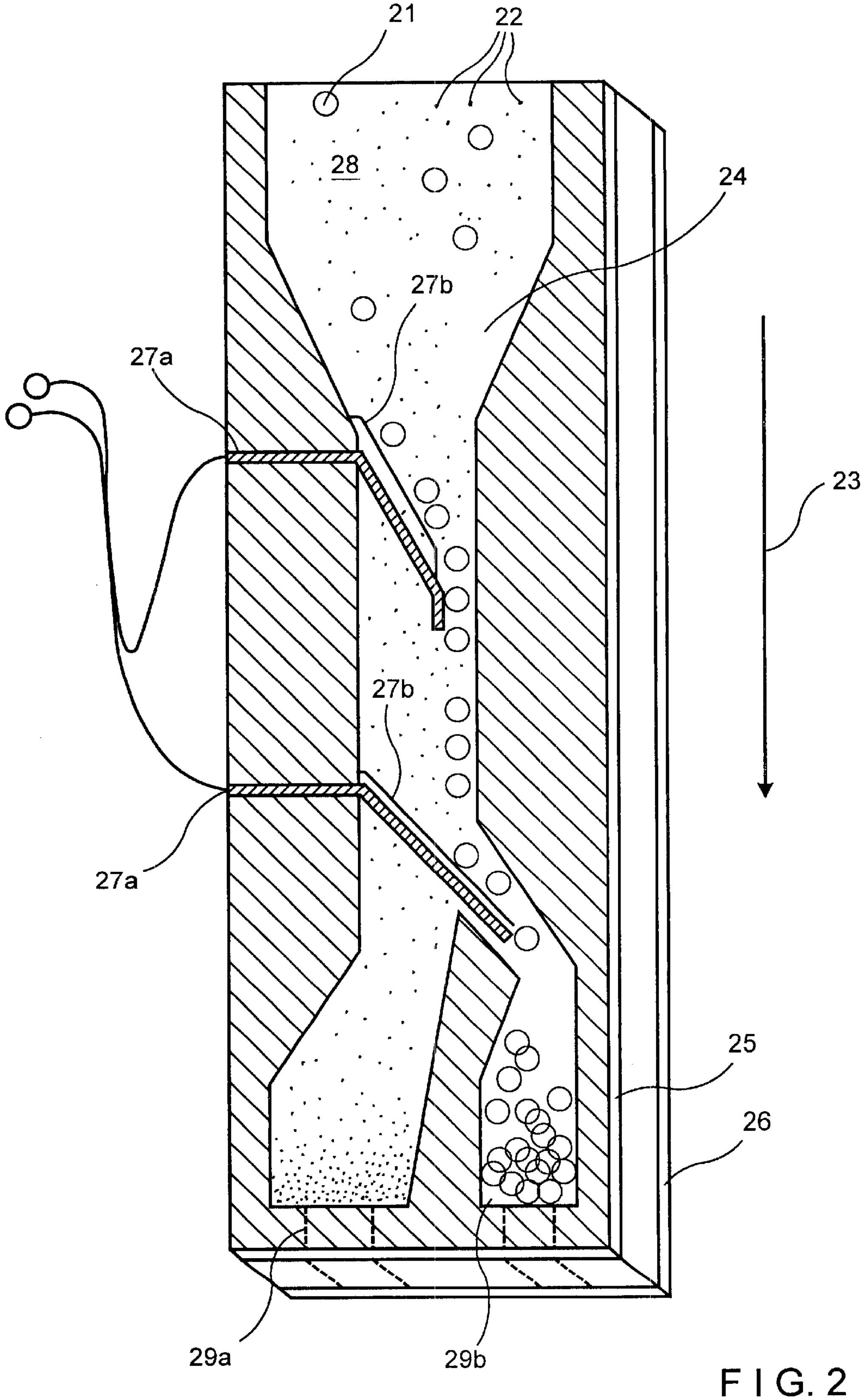
FIG. 2 shows a diagrammatic top view of a microsystem according to the invention adapted for particle separation.

FIG. 2 diagrammatically shows a microsystem for separating a particle mixture comprising larger particles 21 (e.g. cells) and smaller particles 22, present in a suspension. The centrifugal forces act in the direction of the arrow 23 (reference direction). Typical dimensions of the channel structure 24 are as follows:

Width: some 10 μm to some mm (typically: 200–400 μm)

Length: some mm to some cm (typically: 20–50 mm)

Height: some μm to some 100 μm (typically: 50 μm)

On the top 25 and on the bottom 26 of the channel 24, microelectrodes 27*a*, 27*b* are arranged opposite each other. When these microelectrodes are selected with an alternative voltage (as a rule a frequency in the MHz range and an amplitude of some volts), they create field barriers across the channel. By way of negative dielectrophoresis (under certain circumstances also positive dielectrophoresis), said field barriers deflect the particles (the large particles in the case of FIG. 2).

The channel structure 24 extends from the input depot 28 to the closed ends 29*a*, 29*b* of the channel into which said channel, which is straight in the middle section, branches. A first pair of the microelectrodes 27*a*, 27*b* is arranged directly at the end of the input depot 28, which end faces the channel, so as to form a field barrier which protrudes transversely into the channel and which has the task of forcing the large particles 21 into the channel 24 shown on the right in top view. A second pair of the microelectrodes 27*a*, 27*b* is arranged directly in front of the branching-off to the ends 29*a*, 29*b* of the channel; it forms a field barrier which extends transversely across the width of the channel up to the branching-off leading to the channel end 29*b*, said field barrier being provided to guide the large particles 21 to this end of the channel.

A manipulation process according to the invention which in this example is directed to separate the particles, comprises the following steps.

Before centrifugation, the microsystem is filled with a suitable liquid. The microsystem has already been installed in a retainer 12 of the centrifuge (see FIG. 1). But installation can also take place after filling of the microsystem. Shortly before start of centrifugation, the electrodes 27*a*, 27*b* are controlled and in the input depot 28, the suspension of the particles to be separated is added, e.g. by means of a pipetting apparatus. At first, the centrifuge is in idle position, i.e. the microsystem is aligned so as to be vertical or at a slight inclination to vertical. Gravity acting on the particles results in the particles descending at different speeds to the channel structure (sedimentation), with the speed of descent depending on the density of the particles. Depending on the desired particle speed, further movement of the particles towards the ends of the channels is exclusively under the influence of gravity or under the combined influence of gravity and centrifugal forces. Centrifugation can thus be understood to be sedimentation under the influence of an artificially increased acceleration of fall. The moving particles are separated according to their size, by the electrical field of the first pair of microelectrodes.

FIG. 2 shows the conditions during sedimentation or centrifugation. As a result of the centrifugal forces being precisely adjustable via the rotational speed, the particles move to the lower part of the microsystem. According to the usual centrifugation principles, the particles with the highest density sediment first. Since the electrical field barrier in the channel moves the particles 21 to the right, while particles 22 are not influenced by this process, separation of the two particle types into the ends of the channels 29*a*, 29*b* takes place. In addition, the particles in each of the ends of the channels are arranged according to their density as is the case in conventional centrifugation. The microsystem shown can be regarded as a basic form of a device according to the invention. Depending on the application, this basic form can be enlarged, expanded or combined with further microstructures. It provides the advantage that there is no solution flow, while particle movement is nevertheless directed and adjustable. Such systems can also generate movement in the opposite direction if the particles are buoyant.

Starting with the base form shown, a microsystem according to the invention can be extended as desired, as is known per se from dielectrophoretic microsystems. Accordingly, the channel structure may in particular comprise several individual channels, interconnected by means of branch channels. Channels can be straight or curved. Curved channel shapes (e.g. arcs, meanders, curves, angles etc.) can in particular be used to investigate differences in binding between the particles and the channel walls.

According to a further modification, the microsystem can be attached to the retainer 12 (see FIG. 1) so as to be rotatable. During a first centrifugation process, e.g. particle separation according to FIG. 2 takes place in a first orientation of the microsystem. Subsequently, the orientation of the microsystem is changed by 180°, so that gravitational and/or centrifugal forces act in opposite direction to the direction of arrow 23. In this case the ends 29*a*, 29*b* of the channels assume the function of input depots from which further distribution of the separated particles into sub-groups or to treatment (loading with substances, electroporation and similar) can take place if suitable channel structures (additional lateral branch-channels) are present. Depending on the channel structure, changes in orientation other than the 180° reversal are possible. Furthermore it is possible to design the retainer 12 such that the microsystem is rotated during centrifugation.

Figure 3:
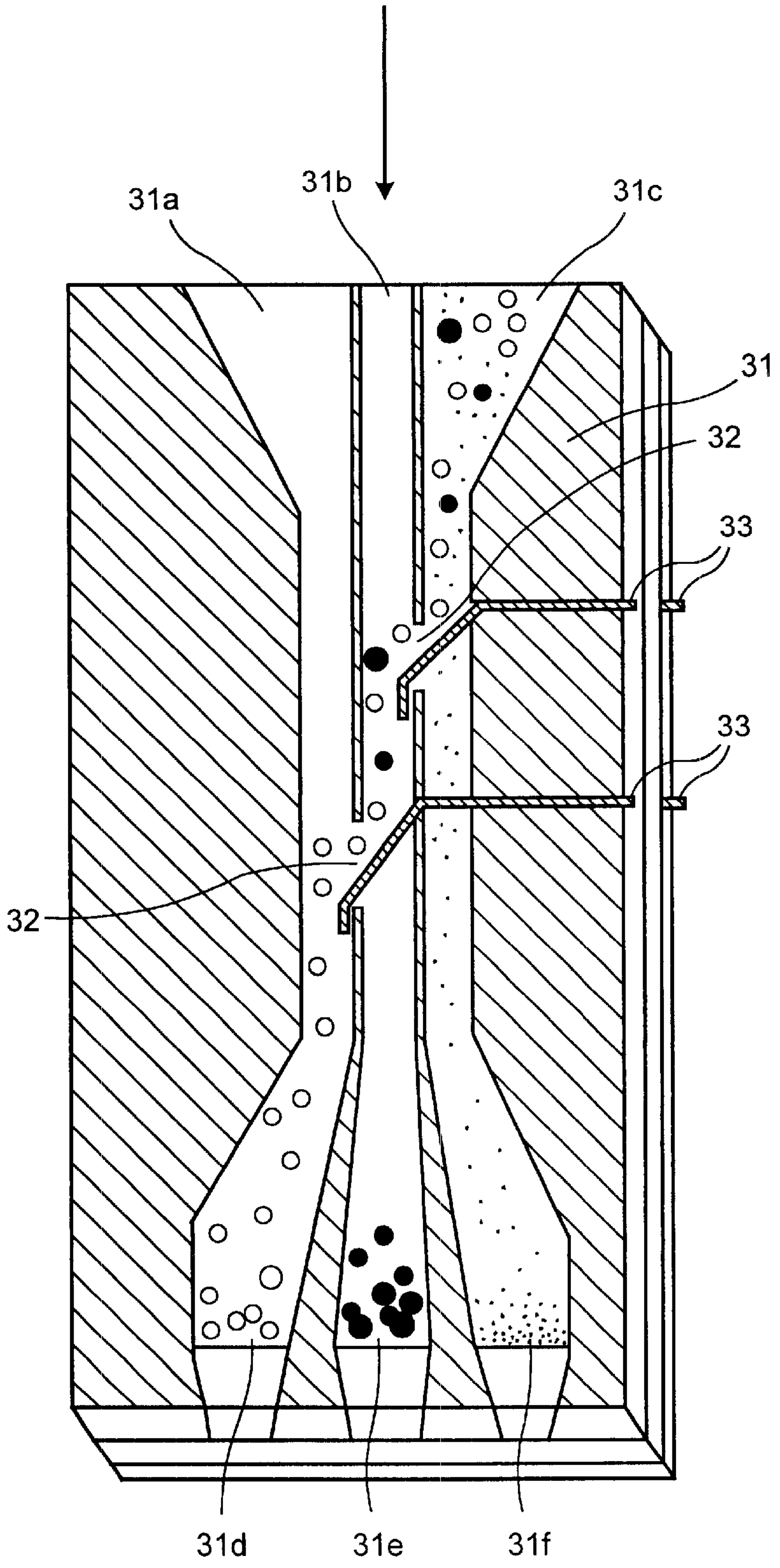
FIG. 3 shows a diagrammatic top view of a programmable loading microsystem according to a further embodiment of the invention.

FIG. 3 shows a further embodiment of the invention, namely a programmable loading-microsystem for cells or particles. In this embodiment the centrifugation channel is divided into three parts 31*a*, 31*b*, 31*c*. In the intermediary walls there are apertures 32 through which again electrodes 33 protrude at the top and bottom of the channel. The apertures are matched to the particle size (typically 5 to 20 times larger than the diameter). At first, each of the parts 31*a* to 31*c* of the channel is filled with various solutions which are used for chemically changing or loading the particles. After this, the particles are inserted into one part of the channel (in the example shown e.g. 31*c*). Through centrifugation, the particles (e.g. first the black ones, then the light ones) move to the electrodes 33 where they can automatically be conveyed via the electrical field barriers to the adjacent solution through the apertures 32.

Here too, sorting into the three channel ends 31*d*, 31*e*, 31*f* and at the same time arrangement of the particles according to their mass density, take place.

The microsystems are further characterised in that they may comprise apertures (inflows, through-flows, outflows) which can be closed off so that after or before centrifugation, the particles can easily be removed or inserted. Furthermore, all the microelectrode elements (holding electrodes for particles, microfield cages etc.) can be installed which are known per se for dielectrophoretic influencing of particles, and which are used in conventional microsystems which operate with flowing liquids. Based on the combined action of gravitational or centrifugal forces with dielectrophoretic forces, the method according to the invention is an electrically controlled or active centrifugation. Furthermore, combinations can be provided with the effect of optical forces (laser tweezers), magnetic forces (influence on magnetic particles), or mechanical forces in the form of ultrasonic forces.

Areas of application of the invention include in particular:

cell separation/cell fractionation;

cell sorting;

cell loading (molecular, nano-particles, beads);

cell discharge (molecular)

cell permeation (so-called electroporation);

cell fusion (so-called electrofusion);

cell pair formation; and cell aggregate formation.

The invention is not limited to particular solution liquids or suspension liquids. It is advantageous if the viscosity of the liquid contained in the microsystem is known. If the viscosity is known, the rotational speed for setting a particular particle speed can be determined on the basis of tabular values or by means of a program algorithm.

Alternatively, it is however also possible to acquire the actual speed of the particles in the microsystem during centrifugation (e.g. by using an optical sensor) and to regulate the rotational speed for setting a particular particle speed. It can be provided that in various sub-sections of the channel structures, e.g. in parallel channels which are interconnected only via an aperture, liquids of various viscosity are contained. In this case however, viscosities are preferred which ensure that diffusion of the liquids through the aperture is relatively low or negligible over the entire period of centrifugation.

If the mass density of the particles is less than that of the liquid in the microsystem, the invention can be implemented with corresponding modifications in that particles are introduced on the side of the microsystem away from the axis of rotation. They then move to the other end of the microsystem under the influence of buoyancy or by the combined effect of buoyancy and centrifugal forces.

The microsystem is designed corresponding to the channel structure and alignment of the electrodes in dependence on the particular application. As a rule, the cross-sectional dimensions of channels are significantly larger than the diameter of individual particles. Advantageously, this prevents blocking of the channels. If only particles with particularly small dimensions have to be manipulated (e.g. bacteria or viruses or cell organelles), then the channel dimensions can be reduced accordingly, e.g. to dimensions below 10 $\mu$m.

The invention is implemented with a microsystem which is closed off at least on one side. The closed end can be a closed-off end of a channel, a closed-off collection zone or a closed-off hollow space in the microsystem. With particle manipulation according to the invention, there is essentially no movement of liquid towards the closed end.

In particular with implementation of collection zones or hollow spaces at the closed-off end, this means that these, like the entire microsystem, are filled with the solution or suspension for the particles at the beginning of particle manipulation.

If during manipulation of the particles, agglomerations or temporary blockages of the channel structures occur, according to the invention it is provided to temporarily increase the rotational speed of the centrifuge so as to detach the adhering particles and move them on.

What is claimed is:

1. A method for manipulating particles in a fluidic microsystem in which the particles are moved in a suspension liquid in a predetermined reference direction, wherein the microsystem has a channel divided into sub-channels or reservoirs each of which have a closed end and point in the reference direction, the method comprising:

moving the particles at a speed set by predetermined centrifugal forces and/or gravitational forces, in the suspension liquid which is stationary in relation to the microsystem, with the centrifugal forces and/or gravitational forces extending essentially parallel to the reference direction; and separating the particles into different sub-channels or reservoirs of the microsystem by creating field barriers across the channel for exposing the particles to at least one particle-specific deflection force;

wherein the direction of the deflection force(s) differs from the reference direction and the deflection force direct particles into one or more sub-channels or reservoirs.

2. The method according to claim 1, in which the microsystem is attached to a swinging rotor centrifuge, with the particle movement at standstill of the oscillatory rotor centrifuge taking place as sedimentation under the influence of gravitational forces and, during operation of the swinging rotor centrifuge, under the effect of centrifugal forces.

3. The method according to claim 1, in which the deflection forces comprise electrical polarisation forces, optical forces, magnetic forces or ultrasonic forces.

4. The method according to claim 3, in which the rotational speed of the swinging rotor centrifuge is set such that the centrifugal forces acting on the particles are smaller than or equal to, the deflection forces.

5. The method according to claim 1, in which several particle movements under the effect of centrifugal forces take place in separate centrifugation steps, with an adjustment of the microsystem to the changed orientation in relation to the centrifugal forces taking place between said centrifugation steps.

6. The method according to claim 1, in which the particles under the influence of buoyancy forces move in the direction opposite to the direction of the centrifugal forces and/or gravitational forces.

7. Method according to claim 1 wherein synthetic and/or biological particles are manipulated for separating, fractionating, sorting, loading, unloading, permeating, fusing, pair forming and/or aggregate forming of said particles.

8. The method according to claim 2, in which the rotational speed of the swinging rotor centrifuge is selected depending on the size or density of the particles.

9. The method according to claim 3, in which the rotational speed of the swinging rotor centrifuge is regulated depending on the speed of the particles which is detected with an optical or electrical sensor.

10. A microsystem comprising a field barrier creating device and at least one channel which extends from an input depot and splits into sub-channels or reservoirs, wherein the microsystem is adapted for affixation to a centrifuge rotor such that during centrifuge operation the centrifugal forces which act on the particles in the channel are essentially aligned parallel to the alignment of the channel;

the ends of the sub-channels or reservoirs are closed or closeable during operation of the centrifuge; and the field barrier creating device is adapted to direct particles into the sub-channels or reservoirs by creating one or more field barriers across the channel for exerting at least one particle-specific deflection force on the particles in the channel in a direction other than the direction of the channel.

11. The microsystem according to claim 10, in which the device for exerting deflection forces is constituted by a microelectrode device which comprises microelectrodes for generating field barriers in the microsystem.

12. The microsystem according to claim 10, which is affixed to the rotor of the centrifuge so as to be swivellable.

13. The microsystem according to claim 10, in which an electronic control of the microsystem is affixed to the rotor of the centrifuge.

14. The microsystem according to claim 11, in which the microelectrodes are arranged on the opposite longitudinal sides of the channel and are adapted for a high-frequency alternative voltage to be applied to them.

15. The microsystem according to claim 14, in which the microelectrodes are band-shaped electrodes which extend transversely to the alignment of the channel and are equipped for generating field barriers in the channel.

* * * * *